US012558130B2

(12) United States Patent
Lubensky et al.

(10) Patent No.: US 12,558,130 B2
(45) Date of Patent: Feb. 24, 2026

(54) BONE ANCHOR HEAD CONVERTER

(71) Applicant: OrthoPediatrics Corp., Warsaw, IN (US)

(72) Inventors: Scott Lubensky, Warsaw, IN (US); Ryan Harper, Warsaw, IN (US); Rebecca Boerigter Lengyel, Fort Wayne, IN (US); David Wayne Daniels, Winona Lake, IN (US); Scott J. Luhmann, Ladue, MO (US)

(73) Assignee: Ortho Pediatrics Corp., Warsaw, IN (US)

( * ) Notice: Subject to any disclaimer, the term of this patent is extended or adjusted under 35 U.S.C. 154(b) by 251 days.

(21) Appl. No.: 17/600,528

(22) PCT Filed: Apr. 2, 2020

(86) PCT No.: PCT/US2020/026477
§ 371 (c)(1),
(2) Date: Sep. 30, 2021

(87) PCT Pub. No.: WO2020/206182
PCT Pub. Date: Oct. 8, 2020

(65) Prior Publication Data
US 2022/0192717 A1 Jun. 23, 2022

Related U.S. Application Data

(60) Provisional application No. 62/828,837, filed on Apr. 3, 2019.

(51) Int. Cl.
A61B 17/70 (2006.01)
A61B 17/86 (2006.01)
(Continued)

(52) U.S. Cl.
CPC ...... A61B 17/7032 (2013.01); A61B 17/8685 (2013.01); A61B 2017/00526 (2013.01)

(58) Field of Classification Search
CPC ............ A61B 17/7032; A61B 17/8685; A61B 2017/00526
(Continued)

(56) References Cited

U.S. PATENT DOCUMENTS 5,667,508 A * 9/1997 Errico ................ A61B 17/7032
606/301
7,766,946 B2 * 8/2010 Bailly ................ A61B 17/7037
606/267
(Continued)

FOREIGN PATENT DOCUMENTS

CA 2772473 A1 * 9/2012 ......... A61B 17/7032
EP 2455031 A2 5/2012
(Continued)

*Primary Examiner* — Eduardo C Robert
*Assistant Examiner* — David C Comstock
(74) *Attorney, Agent, or Firm* — FBT Gibbons LLP; Paul M. Ulrich

(57) ABSTRACT

A pedicle screw tulip head converter. The converter can have a first portion joined to a second portion. The first portion can have a surface parallel to a first portion plane, and an opening defining a first portion axis. The second portion can extend from the first portion and can have a surface parallel to a second portion plane, the second portion plane being perpendicular to the first portion plane. The second portion can have a curved surface that defines a second portion axis, the second portion axis being perpendicular to and coplanar with the first axis.

16 Claims, 8 Drawing Sheets

(51) Int. Cl.
    *A61B 17/88*         (2006.01)
    *A61B 17/00*         (2006.01)

(58) Field of Classification Search
    USPC ....... 606/264–267, 270, 271, 272, 273, 274,
                606/275, 276, 277, 278, 279, 305, 306,
                           606/308, 322, 328
    See application file for complete search history.

(56)                 References Cited

U.S. PATENT DOCUMENTS

| | | | |
|---|---|---|---|
| 8,083,776 B2 * | 12/2011 | Alvarez ............. | A61B 17/7037 |
| | | | 606/305 |
| 10,786,285 B2 * | 9/2020 | Stein ................. | A61B 17/7043 |
| 2001/0012937 A1 | 8/2001 | Schaffler-Wachter et al. | |
| 2004/0097926 A1 * | 5/2004 | Kim ................... | A61B 17/7032 |
| | | | 606/270 |

| | | | |
|---|---|---|---|
| 2005/0215998 A1 | 9/2005 | Donath | |
| 2006/0161153 A1 | 7/2006 | Hawkes et al. | |
| 2007/0073291 A1 | 3/2007 | Cordaro et al. | |
| 2010/0274295 A1 | 10/2010 | Carls et al. | |
| 2012/0209332 A1 * | 8/2012 | Janowski ........... | A61B 17/7082 |
| | | | 606/278 |
| 2017/0348026 A1 * | 12/2017 | Stein .................. | A61B 17/7043 |
| 2018/0153600 A1 * | 6/2018 | Koller .................. | A61B 17/864 |
| 2018/0228516 A1 * | 8/2018 | Armstrong ......... | A61B 17/7035 |
| 2022/0192717 A1 | 6/2022 | Lubensky et al. | |

FOREIGN PATENT DOCUMENTS

| | | | |
|---|---|---|---|
| EP | 2591741 A1 | 5/2013 |
| JP | 2007136196 A | 6/2007 |
| WO | 1999044526 A1 | 9/1999 |
| WO | 2020206182 A1 | 10/2020 |

* cited by examiner

100

107

112

108

112

106

104

110

102

107          106

112          112

116

114          114

108

200

206

208

204

202

210

106

116

114

114

130

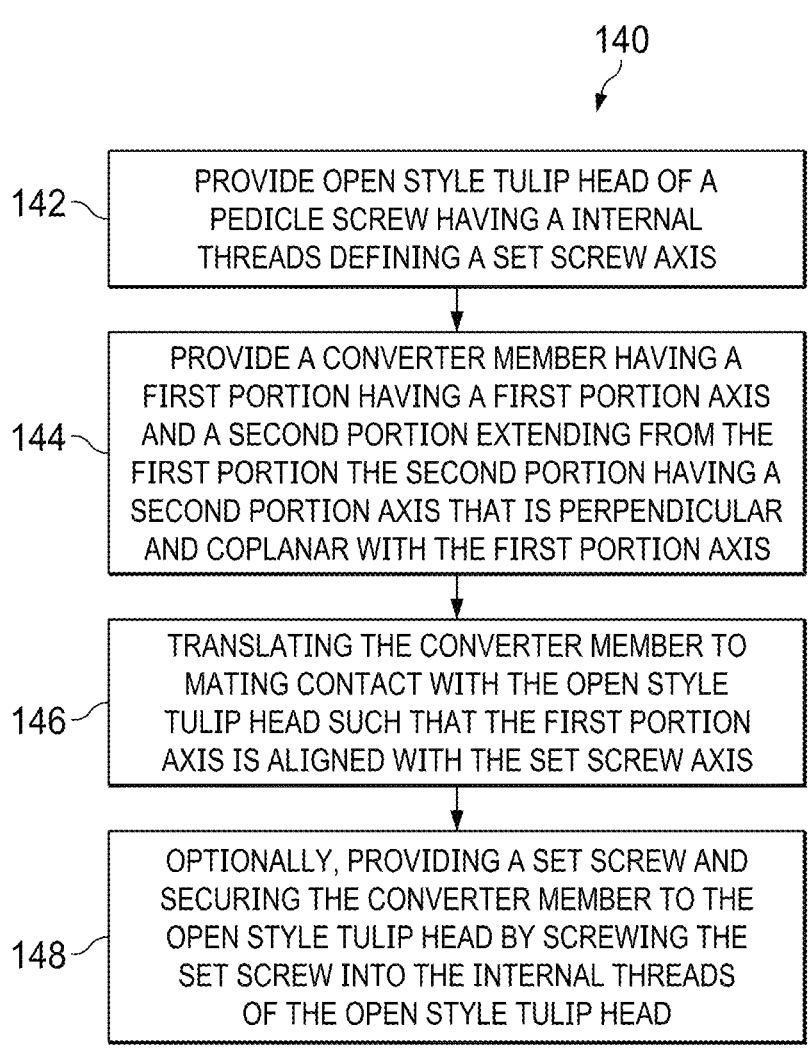

140

142 — PROVIDE OPEN STYLE TULIP HEAD OF A PEDICLE SCREW HAVING A INTERNAL THREADS DEFINING A SET SCREW AXIS

144 — PROVIDE A CONVERTER MEMBER HAVING A FIRST PORTION HAVING A FIRST PORTION AXIS AND A SECOND PORTION EXTENDING FROM THE FIRST PORTION THE SECOND PORTION HAVING A SECOND PORTION AXIS THAT IS PERPENDICULAR AND COPLANAR WITH THE FIRST PORTION AXIS

146 — TRANSLATING THE CONVERTER MEMBER TO MATING CONTACT WITH THE OPEN STYLE TULIP HEAD SUCH THAT THE FIRST PORTION AXIS IS ALIGNED WITH THE SET SCREW AXIS

148 — OPTIONALLY, PROVIDING A SET SCREW AND SECURING THE CONVERTER MEMBER TO THE OPEN STYLE TULIP HEAD BY SCREWING THE SET SCREW INTO THE INTERNAL THREADS OF THE OPEN STYLE TULIP HEAD

FIG. 14

BONE ANCHOR HEAD CONVERTER

CROSS REFERENCE TO RELATED APPLICATION

This application claims the benefit of U.S. Provisional Patent Application Ser. No. 62/828,837, filed on Apr. 3, 2019, and International Patent Application Serial No. PCT/US20/26477, filed on Apr. 2, 2020, both entitled "BONE ANCHOR HEAD CONVERTER," the disclosure of which are hereby incorporated herein by reference in its entirety.

BACKGROUND

Spinal fixation systems may be used to surgically fix, adjust, and/or align the spinal column. One type of spinal fixation system employs a spinal fixation rod for supporting the spine and fixing, adjusting, aligning, and/or fusing all or portions of the spinal column into a desired orientation. Attachment of the spinal fixation rod to the spinal column has been achieved using a variety of vertebral anchors (i.e., bone anchors). Vertebral anchors include screws, hooks, pins, and bolts used to engage the vertebrae and connect the spinal rod to vertebrae. Pedicle screws have been used successfully as vertebral anchors. Bone anchors (e.g., pedicle screws) and connectors in combination with spinal rods can align and correct deformities in the natural spinal alignment as well as repair traumatic injury.

In general, a pedicle screw can have a head with a receiving opening into which a spinal rod can be secured. The open head of a pedicle screw of this type is often referred to as a "tulip head." An open style tulip-head pedicle screw permits a spinal fixation rod to be translated, i.e., "reduced" into the tulip head via the receiving opening after the pedicle screw has been screwed into the pedicle bone. Once reduced, a set screw can be screwed into threads internally disposed in the receiving opening, effectively closing the opening and fixing the spinal fixation rod into the pedicle screw.

Pedicle screws can also be of the "closed head" style, in which the head is not open to receive a rod translated, or reduced, therein. Rather, the screw head has an opening, i.e., a through hole, through which a spinal fixation rod can be fed, and thereby fixed to the pedicle screw. It is believed that closed head style pedicle screws can withstand greater forces exerted by the spinal fixation rod on the pedicle screw. For example, it is believed that closed head style pedicle screws can withstand greater forces exerted by the spinal fixation rod, forces which could cause open tulip style heads to splay, thereby permitting the spinal fixation rod to move out of its fixed position.

At times, a surgeon may wish to utilize a closed style pedicle screw where an open style tulip head has previously been set, i.e., screwed into a portion of the pedicle bone. It can be the case that during the process of spinal fixation it is discovered that an existing open style tulip head is not desirable, but removing it and replacing it with a closed style head can both add additional surgery time and cause additional trauma to the bone during the screw replacement process.

Accordingly, there remains an unmet need for an apparatus, system, and method to provide for improved bone anchors.

SUMMARY

A pedicle screw tulip head converter. The converter can have a first portion joined to a second portion. The first portion can have a surface parallel to a first portion plane, and an opening defining a first portion axis. The second portion can extend from the first portion and can have a surface parallel to a second portion plane, the second portion plane being perpendicular to the first portion plane. The second portion can have a curved surface that defines a second portion axis, the second portion axis being perpendicular to and coplanar with the first axis.

BRIEF DESCRIPTION OF THE DRAWINGS

The present disclosure will be more readily understood from a detailed description of some example embodiments taken in conjunction with the following figures:

FIG. 14 depicts a flow diagram of an embodiment of a method of converting a pedicle screw.

DETAILED DESCRIPTION

Figures 1, 2:
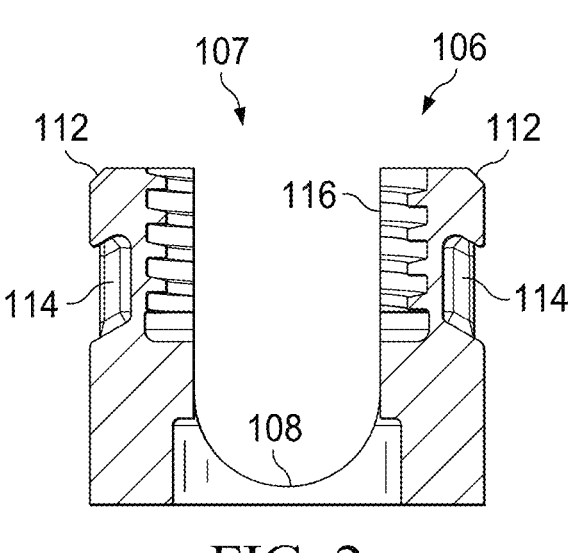
FIG. 1 depicts a side elevation view of a representative open style tulip head pedicle screw.
FIG. 2 depicts a partial cross-sectional view of a representative open style tulip head of a pedicle screw.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Described herein are example embodiments of bone anchors (e.g., anchors, screws, etc.) useful for orthopedic procedures such as, for example, spinal fixation. In the illustrated embodiments a pedicle screw is disclosed to teach the features and benefits of a bone screw, but the disclosure is not to be limited only to pedicle screws, nor are the bone anchor head converters limited to engaging and/or working with only pedicle screws. Such extenders may configured to engage and/or work with any type of bone anchor, both mono-axial and/or polyaxial. As used herein, an "open style" bone anchor is a bone anchor having a "tulip head" in which a spinal fixation rod can be translated into, i.e., reduced into the head through a receiving opening at, for example, the top of the tulip head. One example of an open style bone anchor (or open style pedicle screw) is a pedicle screw having a "tulip head" in which a spinal fixation rod can be translated into, i.e., reduced into the head through a receiving opening at, for example, the top of the tulip head and into channel 107, as described with respect to FIGS. 1-3 herein. As used herein, a "closed style" bone anchor is a bone anchor screw having an opening through which a spinal fixation rod can be fed through a receiving opening at, for example, a side of the tulip head. One example of a "closed style" bone anchor (or closed style pedicle screw) is a pedicle screw having an opening through which a spinal fixation rod can be fed through a receiving opening at, for example, a side of the tulip head, as described with respect to FIG. 4 herein.

Referring to FIG. 1, a representative open style pedicle screw 100 is shown. Open style pedicle screw 100 can be any of known pedicle screws of the type often referred to as having "tulip heads." For the purposes of the present disclosure, the open style pedicle screw is described as including a screw shank 102, a neck 104, a head 106, which is often referred to as a tulip head 106. The tulip head 106 can include first and second tulip arms 112 opposed from each other. First and second tulip arms can form a channel 107. First and second tulip arms 112 can extend from a curved lower surface (e.g., rod seat 108) defining the substantially U-shaped interior channel 107. The channel 107 can be constructed to receive a spinal fixation rod (e.g., 122) and can include a channel axis. The channel axis can correspond to, and be coincident with, a longitudinal axis of a spinal fixation rod when it is reduced into the channel 107. The rod 122 can be reduced into the channel 107 until it rests on a portion of the open channel surface, e.g., the rod seat 108. The shank can have an inner diameter and an outer diameter, the inner diameter and outer diameter each being determined by the size of the screw and the depth of threads 110 on shank 102. The thread depth, pitch, and other dimensional features can be predetermined based on the requirements of the pedicle screw, as is known in the art. That is, the proportions of the bone screw depicted are for illustrative purposes only and variations in the length of the shank, diameter of the screw, thread pitch, thread length, number of thread leads, shank induced compression and the like may be varied without departing from the scope of the disclosure.

Other components and features of an open style pedicle screw can be included that aid in insertion and use of the pedicle screw, including spinal fixation rod reduction. For example, as depicted in the partial cross-sectional view of tulip head 106 in FIG. 2, tulip head 106 can include features for compatible operation with driving tool (not shown) and a rod reduction device (not shown). As a specific example, a rod reduction device, as is known in the art, may be used to engage with tulip head 106 to urge, or reduce, a spinal fixation rod into the channel 107 and toward the rod seat 108, manipulate one or more vertebrae, and/or insert a set screw for temporary or stationary fixation of the spinal rod into the pedicle screw tulip head 106. For this reason, tulip head 106 can have various features, such as grasping tabs 112 and/or pockets 114, for connectivity and operation of the driving tool and/or rod reducing tool, and internal threads 116 for receiving a set screw.

Figure 3:
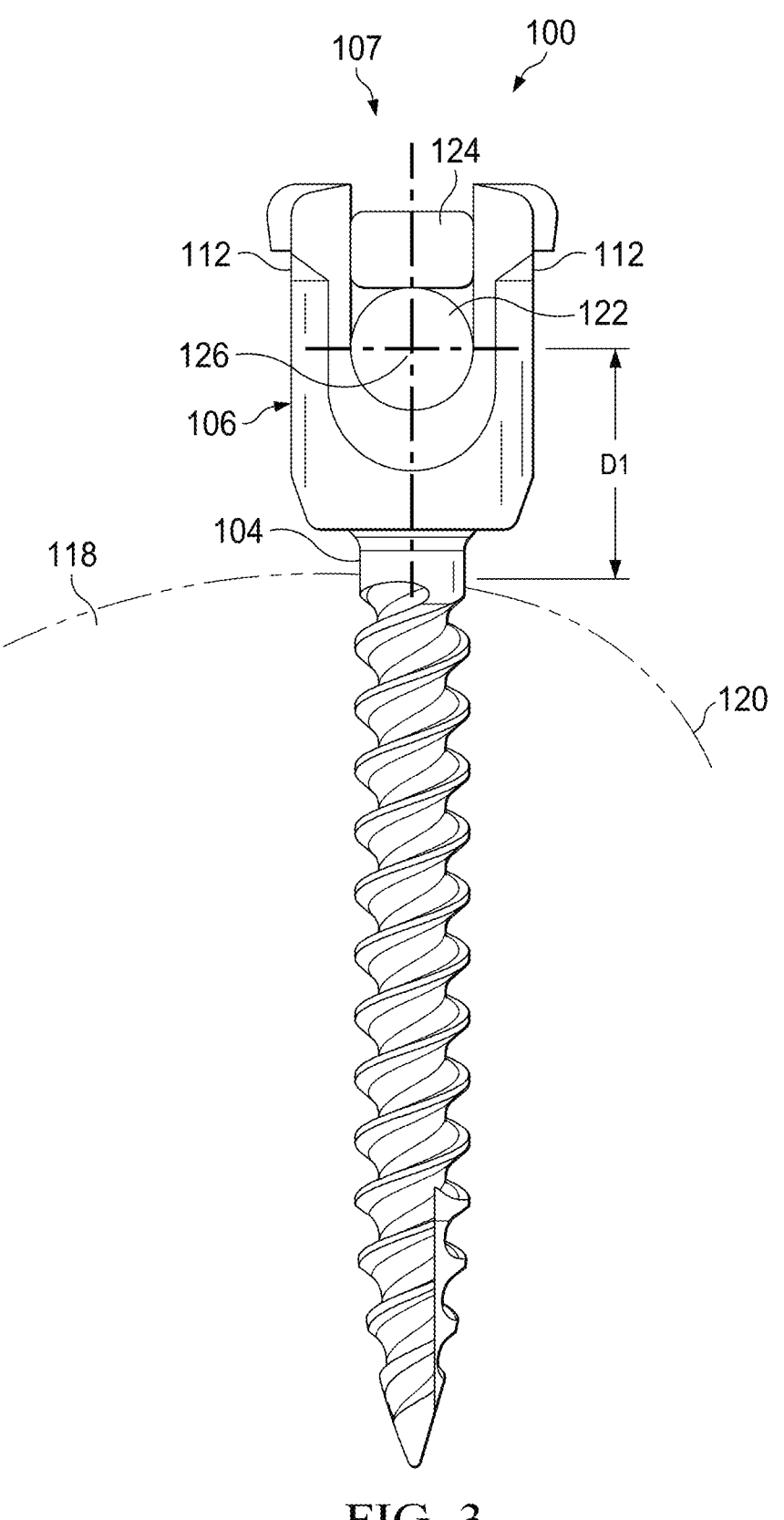
FIG. 3 depicts a schematic representation of one example of an open style tulip head pedicle screw installed in a bone.

Referring now to FIG. 3, there is shown an open style pedicle screw 100 screwed into a bone 118, the surface of which is representatively depicted by the dashed line 120. Bone 118 can be a pedicle, and pedicle screw 100 can be driven into the pedicle until the neck 104 is adjacent the bone 118. In an embodiment, the pedicle can be undertapped for the appropriate screw size. After the pedicle is undertapped a flexible feeler probe may be used to verify presence of threads in the tapped hole. To measure the length of the hole, a feeler probe is advanced to the floor of the hole and a hemostat is clamped to the feeler probe at the point where it exits the pedicle. The appropriate screw diameter and length may subsequently be selected based on both preoperative measurement and intraoperative observation. The same technique can be repeated for any remaining pedicles that need to be instrumented.

A rod reduction tool can be applied over the tulip head 106 of the screw. In an embodiment, fingers of the rod reduction device can engage the pockets 114 of the pedicle screw tulip head 106. The rod 122 can then be reduced by the rod reduction device to set in rod seat 108. A set screw driver can then be used to introduce a set screw 124. The set screw can be passed through the rod reduction device and rotated until it bottoms out, securing rod 122 into the tulip head 106.

As depicted in FIG. 3, once rod 122 is reduced into tulip head 106 and set screw 124 is set, the distance D1 from bone surface 120 and the axial center 126 of rod 122 is immovably fixed. However, due to spinal curvature or other forces imposed on the spinal fixation rod 122, the spinal fixation rod 122 can have exerted thereon forces against the set screw 124 (upwardly as depicted in FIG. 3). If the forces exerted against set screw 124 become too great the set screw can fail, thereby allowing the spinal fixation rod 122 to move out of place. Another mode of failure can be splaying of the tulip head, which also results in loss threaded connection of the set screw 124, and loss of placement of the spinal fixation rod 124.

Figure 4:
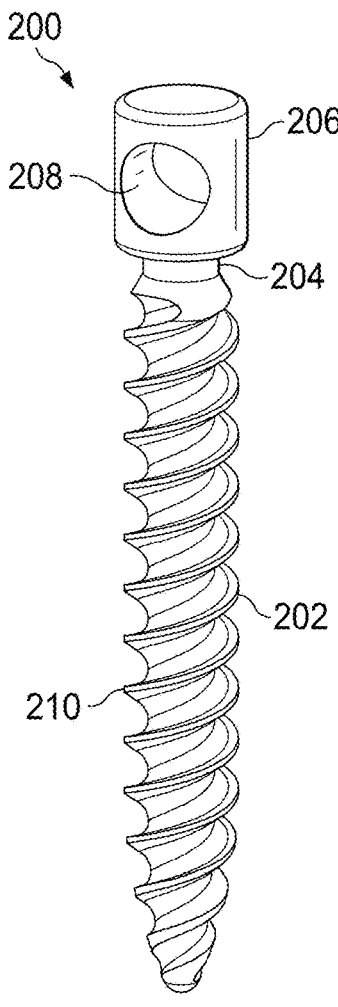
FIG. 4 depicts a perspective view of one example of a closed style pedicle screw of the present disclosure.

Referring to FIG. 4 there is shown a representative embodiment of a closed style pedicle screw 200. For the purposes of the present disclosure, the closed style pedicle screw is described as including a screw shank 202, a neck 204, and a head 206. The head 206, rather than being an open tulip style head, is a closed head that includes a through hole opening 208 disposed therethrough. This through hole opening 208 can allow a spinal fixation rod to be fed into, fed through, and ultimately, secured to the pedicle screw 200. As discussed above, for closed style pedicle screws, the shank can have an inner diameter and an outer diameter, the inner diameter and outer diameter each being determined by the size of the screw and the depth of threads 210 on shank 202. The thread depth, pitch, and other dimensional features can be predetermined based on the requirements of the pedicle screw, as is known in the art. That is, the proportions of the bone screw depicted are for illustrative purposes only and variations in the length of the shank, diameter of the screw, thread pitch, thread length, number of thread leads, shank induced compression and the like may be varied without departing from the scope of the disclosure. As can be understood, although more difficult to work with, the closed style pedicle screw head can completely surround the spinal fixation rod 124, thereby alleviating one or more of the problems of set screw failure discussed above with respect to open style pedicle screw heads.

Figure 5:
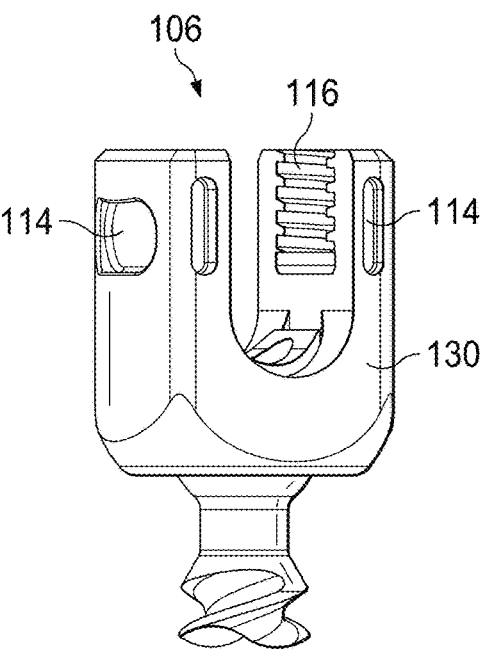
FIG. 5 depicts a partial perspective view of one example of an open style tulip head pedicle screw of the present disclosure.

Referring to FIG. 5, there is shown an example embodiment of an open style pedicle tulip head 106 showing representative features that can be used for connectivity and operation, and can be intended on such a screw to facilitate the driving tool and/or rod reducing tool. For the present disclosure such features, and any other features of their kind, can be utilized to facilitate conversion of an open style pedicle screw to a closed style pedicle screw. As shown in FIG. 5, for example, an open style pedicle tulip head 106 can have internal threads 116 and indented portions, referred to herein as pockets 114 on various lateral surfaces 130 of the open style pedicle tulip head 106. As will be more fully understood in light of the description below, pockets 114 can be utilized for secondary purposes, i.e., to facilitate the conversion of an open style pedicle screw into a pedicle screw having a closed head. Other types of open style bone anchors, e.g., open style bone hooks, may include one or more similar and/or the same features as described above with reference to the pedicle screw 100.

In illustrated embodiments of the present disclosure a converter member is disclosed that can be joined to an open style tulip head of a bone anchor. The term "joined" or its derivatives means operatively mated in a connecting manner such that an open style tulip head is converted to operate as a closed style pedicle screw head. Joining can be by adhesive, press fit, snap fit, threaded screw fit, and the like. In an embodiment, converter member can be snap fit by having extensions (not shown) that snap into pockets to securely hold converter member to open style tulip head. In an embodiment, converter member has dimensions designed for a particular open style tulip head such that portions can elastically extend over the top of the tulip head and, when pushed sufficiently down, snap into one or more pockets.

In an embodiment, a converter member can be an integral unit, except for embodiments in which a second portion set screw is utilized, as described below. That is, converter member can be a single piece unit that can be, for example, made of molded polymer. In an embodiment converter member can be injection molded of a polymer material suitable for use in a human body. In general, the converter member can be smooth sided, having smooth contours. In the illustrated embodiments, terms such as "vertical," "upper," "lower" "upwardly," and "downwardly" are used in relation to the converter member in the orientation shown in the FIGS, and corresponding to the orientation generally experienced and understood in the use of pedicle screws and related instrumentation. Likewise, for descriptive purposes various planes are referred in describing relative orientations of features and surfaces. However, the term "plane" is not intended to imply any flatness, smoothness, or other planar characteristics to the features and surfaces so described.

Figure 6:
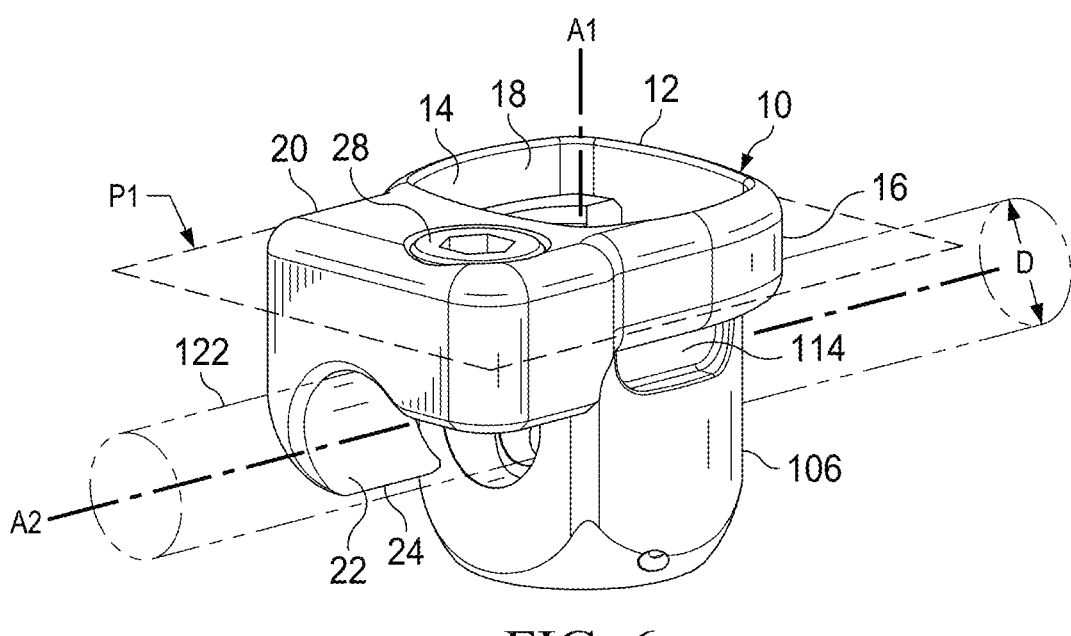
FIG. 6 depicts a perspective view of one example of a converter member of the present disclosure.

Referring now to FIG. 6, a converter member 10 is disclosed that can be joined to an open style tulip head 106 to convert the bone anchor (e.g., pedicle screw) to a bone anchor having the benefits of a closed style bone anchor. Once converted, a bone anchor can be considered a closed style bone anchor (e.g., closed style pedicle screw). The converter member 10 can be joined to open style tulip head 106 by insertion and tightening of a set screw (not shown, but such as, for example the set screw described below) in the direction of axis A1 that engages the internal threads 116, or can be snap fit onto tulip head 106 by having extensions (not shown) that snap into pockets 114 to securely hold converter member 10 to open style tulip head 106. Axis A1 can correspond to the longitudinal axis of the tulip head pedicle screw, as can be understood from the description herein. Once converted, an open style pedicle tulip head 106 can securely hold a spinal fixation rod 122 in a manner having the benefits of a closed style pedicle screw. In some embodiments, converter member 10 effectively surrounds and secures the tulip head portions of the open style tulip head 106 to prevent splaying under forces imparted by the spinal fixation rod 122. Splaying can cause set screw 124 to loosen or release, thereby allowing spinal fixation rod 122 to move or spring free from the pedicle tulip head 106.

In an embodiment, converter member 10 can be a unitary member having two operative portions that can be distinguished by intersecting longitudinally axially oriented openings. A first portion 12 can be defined as the part of converter member 10 that at least partially surrounds a first portion axis A1, which in operation is associated with a longitudinal axis of the internal threads 116 for set screw 124 of tulip head 106. First portion axis A1 can be coaxial with the set screw 124 opening of tulip head 106. Second portion 20 can be defined as the part of converter member 10 that extends from, and can be integral with, first portion 12, and at least partially surrounds a second portion axis A2, which in operation is associated with the longitudinal axis of spinal fixation rod 122. When in use, axis A2 can be coaxial with the axis of spinal fixation rod 122. First portion axis A1 can be perpendicular and co-planar with second portion axis A2.

Figure 7:
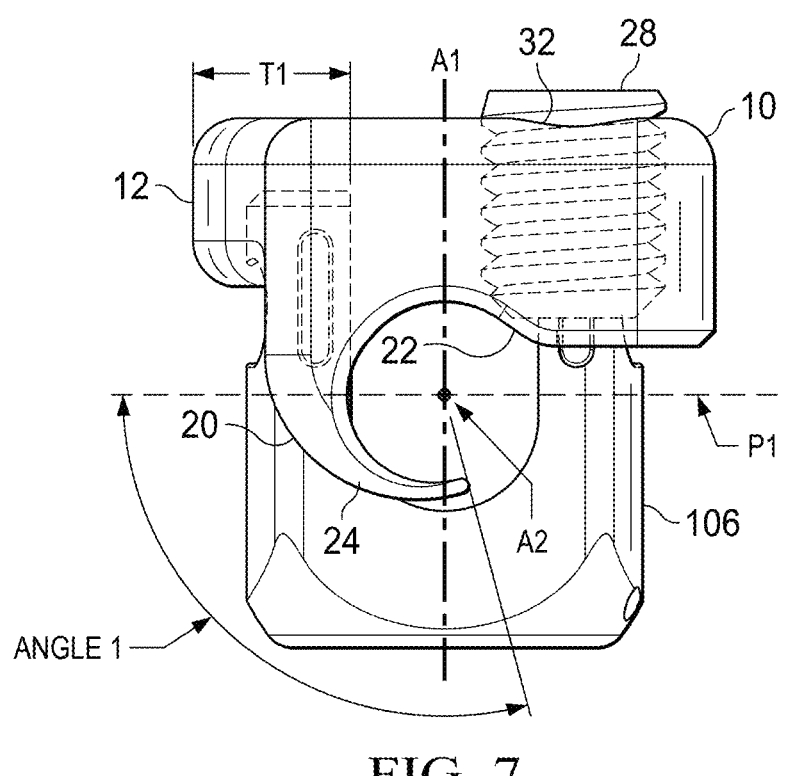
FIG. 7 depicts a side view of one example of a converter member of the present disclosure.

First portion 12 can be a ring-like member having an inner surface 14 and an outer surface 16, the inner and outer surfaces being separated by a first portion thickness that can vary but has an average dimension T1, as indicated in FIG. 7. Inner surface 14 can define a closed perimeter with at least a portion of the inner surface having a dimension greater than the outer dimension of tulip head 106 and which can securely fit over the upper portion of tulip head 106. First portion 12 can have extensions that snap into pockets 114 to join converter member 10 to tulip head 106. The closed perimeter of inner surface 14 defines an opening 18 that surrounds first portion axis A1, which in use can be coaxial with the set screw axis of tulip head 106. That is, first portion axis A1 can be considered to be oriented generally vertically. In an embodiment, tulip head set screw 124 (not shown) can be secured through first portion 12 of converter member 10 to internal threads 116 of tulip head for securement, or additional securement, to join the converter member 10 to tulip head 106. The tulip head set screw 124 can be effectively counter-sunk into the first portion 12 of converter member 10 and provide for secure joining of the converter member 10 to the tulip head 106. Tulip head set screw 124 can additionally supply securement forces against spinal fixation rod 124.

Second portion 20 can extend laterally from first portion 12 and can include a shaped surface 22 for contacting and additional securement of spinal fixation rod 122. The shaped surface 22 can be a generally smooth, partial cylindrical-shaped surface defining a second portion axis A2. The shaped surface 22 can have dimensions that enable close contact with the spinal fixation rod 122 when joined to a tulip head 106.

As shown in the side view of FIG. 7, in an embodiment, shaped surface 22 can have a shaped extension 24 that wraps a distance sufficient to traverse at least an included angle ANG1 of from 10 degrees to 90 degrees measured from a plane P1 in which lies second portion axis A2 and which is perpendicular to axis A1 to a distal end of the shaped extension 24. As can be understood from the description herein, shaped extension can partially wrap spinal fixation rod 122 when converter member 10 is seated and joined to tulip head 106.

Additionally, in an embodiment as shown in FIGS. 6 and 7, second portion 20 can have a second portion threaded opening 32 in which a second portion set screw 28 can be threaded down, i.e., screwed into second portion internal threads 30. Second portion threaded opening 32 can be positioned on second portion 20 such that a portion of the opening where it exits the lower surface of second portion 20 resides where the surface of spinal fixation rod 122 sits when converter member 10 is set in operation. In this manner, when second portion set screw 28 is tightened it may contact and seats against the surface of the spinal fixation rod 122 for additional secure connection of spinal fixation rod 122.

As can be understood from the description of the embodiment of FIGS. 6 and 7, when converter member 10 is utilized on an open style tulip head 106, spinal fixation rod 122 can be completely enclosed by a portion of the tulip head 106, specifically rod seat 108, portions of tulip arms 112, and/or the shaped surface 22 of converter member 10. Shaped extension 24 can provide additional enclosed coverage of converter member 10 for added securement of spinal fixation rod 122. In this manner converter member 10 effectively converts an open style tulip head 106 pedicle screw into a pedicle screw having a closed head. Converter member 10 as described can reduce or eliminate the chances of the tulip head splaying, or the set screw 124 becoming loosened under forces exerted by spinal fixation rod 122.

In a method of use of the embodiment of a converter member 10 shown in FIGS. 6 and 7, a spinal fixation rod 122 can be reduced into a tulip head in any known manner. Once spinal fixation rod 122 is reduced, or close to final reduction, converter member 10 can be placed over and pressed, snapped, screwed, or otherwise engaged, seated, and/or connected onto tulip head 106. In an embodiment, converter member 10 can be closely spaced, but not completely seated on tulip head 106. In an embodiment, shaped extension 24 can be urged around and/or partially under spinal fixation rod 122 during placement of converter member 10 on tulip head 106. Once converter member 10 is placed on tulip head

106 and positioned in place with respect to spinal fixation rod 122, one or both of tulip head set screw 124 and second portion set screw 28 can be tightened down for final fixation and conversion of an open style tulip head pedicle screw to a pedicle screw having a closed head.

Figures 8, 9:
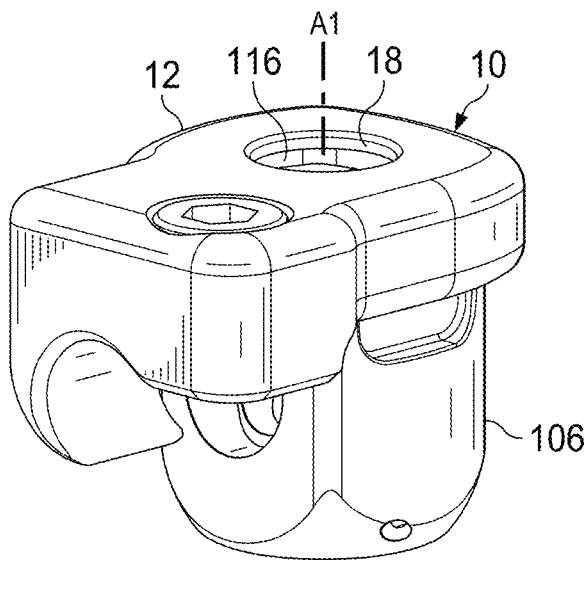
FIG. 8 depicts a perspective view of one example of a converter member of the present disclosure.
FIG. 9 depicts a perspective view of one example of a converter member of the present disclosure.

Referring now to FIG. 8, there is shown a converter member 10 that is similar in most respects to the converter member 10 described above with reference to FIGS. 6 and 7. For conciseness, the description of common elements will not be repeated. As shown in FIG. 8, first portion 12 can have an upper surface that defines an opening 18 that surrounds a first portion axis A1, which in use can be coaxial with the longitudinal axis of internal threads 116 of tulip head set screw 124 (not shown) of tulip head 106. In the embodiment shown in FIG. 8, tulip head set screw 124 can be driven along coaxially with axis A1 through opening 18 and can connect and/or secure converter member 10 to tulip head 106. In an embodiment, the perimeter of opening 18 can also have internal threads that can work in conjunction with the internal threads 116 of tulip head 106.

Referring now to FIG. 9, in an embodiment converter member 10 can have a generally saddle-shaped, full-lobed configuration. Saddle-shaped, full-lobed converter member 10 can be a unitary member having two operative portions that can be distinguished by intersecting axially oriented openings. A first portion 12 can be defined as having a surface substantially parallel to a first portion plane P2, and which is the part of saddle-shaped, full-lobed converter member 10 that defines a first portion opening 18 that at least partially surrounds a first portion axis A1, which in operation is associated with a longitudinal axis of tulip head set screw 124 (not shown) and is perpendicular to first portion plane P2. A second portion 20 can include at least one, and can have one or more lobes (e.g., a first lobe 20A and a second lobe 20B), with each lobe extending downwardly in a spaced, substantially parallel relationship, from first portion 12 and having a surface substantially parallel to a second portion plane P3, and each having a shaped surface 22. In an embodiment, the shaped surface 22 can have a closed perimeter defining an enclosed opening 32 through which spinal fixation rod 122 can be inserted and secured. Second portion plane P3 can be perpendicular to first portion plane P2 and second portion axis A2.

In an embodiment, tulip head set screw 124 can be secured through first portion opening 18 of first portion 12 of saddle-shaped, full-lobed converter member 10 to internal threads 116 of tulip head for securement, or additional securement, to join and/or secure the converter member 10 to tulip head 106. The tulip head set screw 124 can be effectively counter-sunk into the first portion 12 of converter member 10 and provide for secure joining of the converter member 10 to the tulip head 106. Tulip head set screw 124 can additionally supply securement forces against spinal fixation rod 124. In an embodiment, the perimeter of opening 18 can also have internal threads that can work in conjunction with the internal threads 116 of tulip head 106.

In operation, first portion 12 of saddle-shaped, full-lobed converter member 10 can cover and partially surround the top of tulip head 106. When installed on a tulip head 106, as shown in FIG. 9, first portion axis A1 can be coaxial with the tulip head set screw 124 (not shown). Second portion 20 can be defined as the part of saddle shaped, full-lobed converter member 10 that defines at least one, and can be two, lobe openings 34, each lobe opening at least partially surrounding and defining a second portion axis A2, which in operation is associated with the longitudinal axis of spinal fixation rod 122. When in use, second portion axis A2 can be coaxial with the longitudinal axis of spinal fixation rod 122. First portion axis A1 can be perpendicular and co-planar with second portion axis A2.

First portion 12 of saddle-shaped, full-lobed converter member 10 can seat on top of tulip head 106, having a portion that surrounds tulip head 106 to prevent splaying of tulip head 106 when forces from spinal fixation rod 122 are upward. Second portion 20 of saddle-shaped converter member 10 can include one or two downward-oriented partial or full lobes (shown as full first and second lobes 20A and/or 20B) that can be substantially parallel to a plane that can be perpendicular to axis A2.

In a method of securing a spinal fixation rod 122, saddle-shaped, full-lobed converter member 10 can be engaged and/or secured to a spinal fixation rod 122 by inserting spinal fixation rod 122 through opening(s) 32 through first lobe 20A and/or second lobe 20B. Once spinal fixation rod 122 is inserted or threaded through opening(s) 32, saddle-shaped converter member 10 can be placed on and over tulip head 106, aligning axis A1 with the tulip head set longitudinal axis. Once saddle-shaped converter member 10 is placed onto tulip head 106, a tulip head set screw 124 (not shown) can be screwed into internal threads 116, and tightened down for final fixation and conversion of an open style tulip pedicle screw to a pedicle screw having a closed head.

Figure 10:
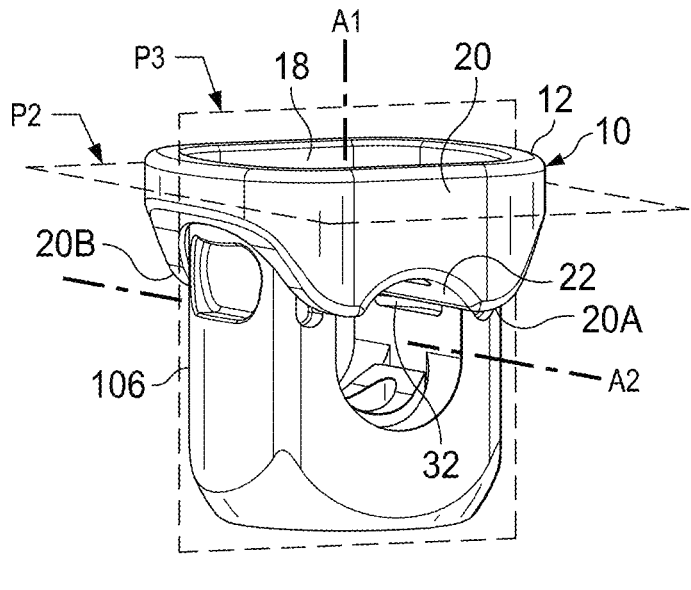
FIG. 10 depicts a perspective view of one example of a converter member of the present disclosure.

Referring now to FIG. 10 there is shown a saddle-shaped, partial-lobed converter member 10 that is similar in most respects to the saddle-shaped, full-lobed converter member 10 described above with reference to FIG. 9. For conciseness, the description of all the common elements will not be repeated. As shown in FIG. 10, first portion 12 can have an upper surface that defines opening 18 that surrounds and is perpendicular to a first portion axis A1, which in use can be coaxial with the longitudinal axis of tulip head set screw 124 (not shown) of tulip head 106. In the embodiment shown in FIG. 10, tulip head set screw 124 can be driven coaxially along axis A1 through opening 18 and can secure converter member 10 to tulip head 106.

Saddle-shaped, partial-lobed converter member 10 can be a unitary member having two operative portions that can be distinguished by intersecting axially oriented openings or shaped surfaces. A first portion 12 can be defined as the part of saddle-shaped, partial-lobed converter member 10 that at least partially surrounds a first portion axis A1, and which in operation is associated with a longitudinal axis of tulip head set screw 124 (not shown). In an embodiment, tulip head set screw 124 can be secured through first portion 12 of saddle-shaped, partial-lobed converter member 10 to internal threads 116 (not shown) of tulip head 106 for securement, or additional securement, to join the saddle-shaped, partial-lobed converter member 10 to tulip head 106. The tulip head set screw 124 can be effectively counter-sunk into a counter-sunk first portion 12 of saddle-shaped, partial-lobed converter member 10 and provide for secure joining of the saddle-shaped, partial-lobed converter member 10 to the tulip head 106. Tulip head set screw 124 can additionally supply securement forces against movement of spinal fixation rod 124.

First portion 12 of saddle-shaped, partial-lobed converter member 10 can seat on top of tulip head 106 to engage and/or at least assist in securing the converter member 10 to the tulip head, and can have a portion that surrounds tulip head 106 to prevent splaying of tulip head 106 when forces from spinal fixation rod 122 are upward. Second portion 20 of saddle-shaped converter member 10 can include one or two downward-oriented lobes 20A and 20B, with each lobe defining a shaped surface 22 that can, in operation, be in contact with spinal fixation rod 122. Second portion 20 can include at least one lobe 20A, and can have two lobes 20A and 20B, with each lobe having a surface substantially parallel to a second portion plane P3, and each having a shaped surface 22, with the shaped surface 22 defining a partial perimeter of opening 32 through which spinal fixation rod 122 can be secured. Second portion plane P3 can be perpendicular to first portion plane P2 and parallel to axis A1.

In a method of securing a spinal fixation rod 122, saddle-shaped, partial-lobed converter member 10 can be placed over tulip head 106 and onto spinal fixation rod 122 until one or more of lobes 20A or 20B contact spinal fixation rod 122. Once saddle-shaped, partial-lobed converter member 10 is placed onto tulip head 106, a tulip head set screw 124 (not shown) can be screwed into internal threads 116, and tightened down for final fixation and conversion of an open style tulip head pedicle screw to a pedicle screw having a closed head.

In operation, first portion 12 of saddle-shaped, partial-lobed converter member 10 covers and at least partially surrounds the top of tulip head 106 as shown, for example, in FIG. 10. When installed on a tulip head 106, as shown in FIG. 10, first portion axis A1 can be coaxial with the tulip head set screw 124 (not shown). Further, when installed, axis A2 can be coaxial with the longitudinal axis of spinal fixation rod 122 (not shown). First portion axis A1 can be perpendicular and co-planar with second portion axis A2. As can be understood from the above description, when operatively installed, saddle-shaped, partial-lobed converter member 10 converts an open style tulip head pedicle screw to a pedicle screw having a closed head.

Figure 11:
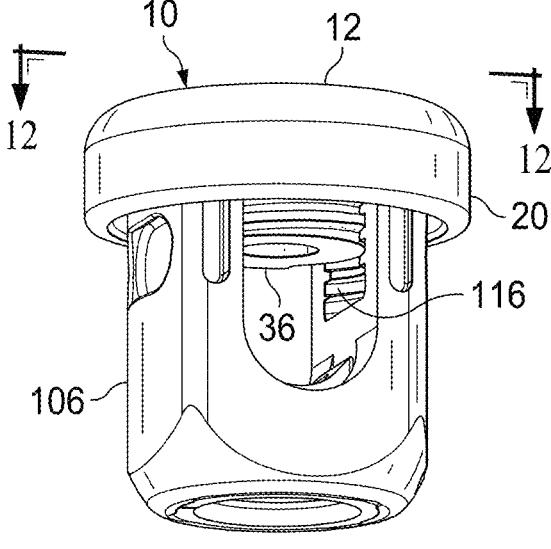
FIG. 11 depicts a perspective view of one example of a converter member of the present disclosure.

Referring now to FIG. 11 there is shown an embodiment of a cap-style converter member 10 that can be screwed onto the top of tulip head 106. In a sense, cap-style converter member 10 can be considered a tulip head set screw 124 replacement, but includes additional features that facilitate the conversion of an open style tulip head pedicle screw to a pedicle screw having a closed head.

Figure 12:
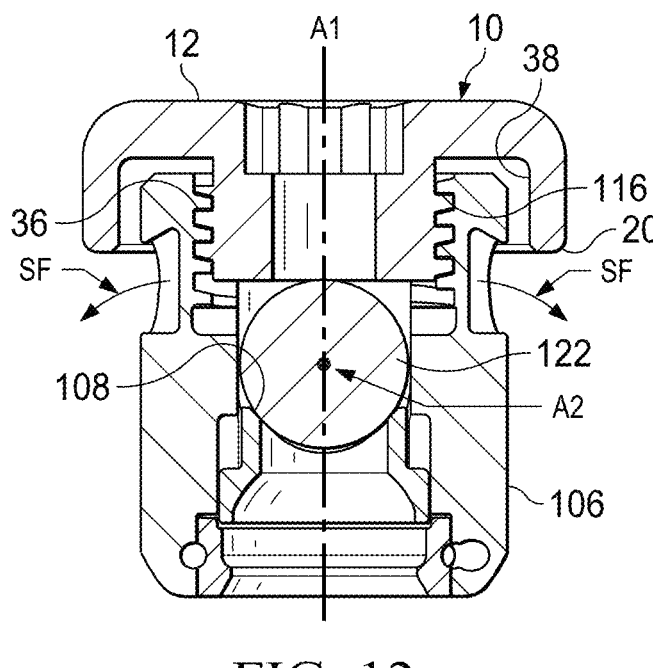
FIG. 12 depicts a cross-sectional view of Section 12-12 of FIG. 11.

As shown in FIG. 11 and the cross-section of FIG. 12, cap-style converter member 10 can have a first portion 12 that can cover and partially surround tulip head 106. A second portion 20 can be a generally circular-shaped lip that surrounds tulip head 106 and can prevent splaying forces SF from opening tulip head 106 upon forces exerted by spinal fixation rod 122. Cap-style converter member 10 can have external threads 36 extending downwardly from first portion 12 and interiorly to second portion 20 lip, and spaced inwardly a sufficient distance to permit a portion of tulip head 106 to extend between external threads 36 and an interior surface 38 of circular-shaped lip. External threads 36 can mate and thread into tulip head internal threads 116 such that cap-style converter member 10 can be screwed down onto, into, and over tulip head 106, thus securing spinal fixation rod 122 for final fixation and conversion of an open style tulip head pedicle screw to a pedicle screw having a closed head.

In a method of securing a spinal fixation rod 122, cap-style converter member 10 can be placed over tulip head 106 and screwed onto tulip head 106 with the circular-shaped lip being external to the tulip head 106. Once cap-style converter member 10 is screwed onto tulip head 106, it can be tightened down for final fixation and conversion of an open style tulip head pedicle screw to a pedicle screw having a closed head.

Figure 13:
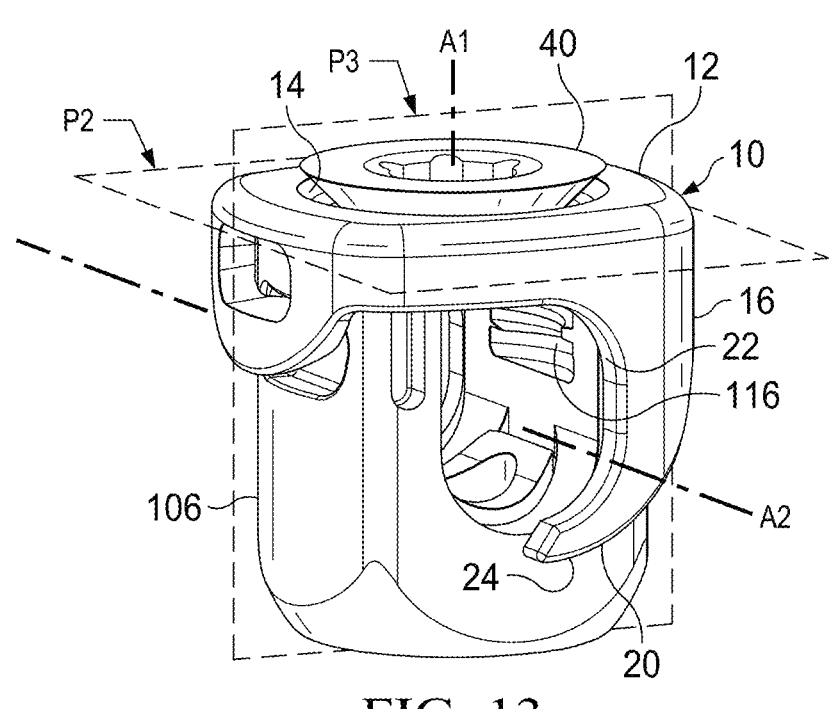
FIG. 13 depicts a perspective view of one example of a converter member of the present disclosure.

Referring now to FIG. 13, there is shown an embodiment of a converter member that can be snapped into place on a tulip head 106 and/or screwed into place via a set screw 40 that can be, in an embodiment, tulip head set screw 124. Like the embodiments discussed above, the converter member 10 illustrated in FIG. 13 can be a unitary member having two operative portions that can be distinguished by intersecting axially oriented openings. A first portion 12 can be defined as the part of converter member 10 that at least partially surrounds a first portion axis A1, which in operation is associated with a longitudinal axis of tulip head internal threads 116 and/or set screw 124 of tulip head 106. In operation, first portion axis A1 can be coaxial with the set screw 124 opening of tulip head 106. Second portion 20 can be defined as the part of converter member 10 that extends downwardly from first portion 12 and at least partially surrounds and defines a second portion axis A2, which in operation is associated with the longitudinal axis of spinal fixation rod 122. When in use, axis A2 can be coaxial with the longitudinal axis of spinal fixation rod 122. First portion axis A1 can be perpendicular with and co-planar with second portion axis A2.

First portion 12 can be a ring-like member having an upper surface parallel to a first portion plane P2, an inner surface 14 and an outer surface 16, the inner and outer surfaces being separated by a first portion thickness that can vary but has an average dimension T1 (similar to that shown in FIG. 7). Inner surface 14 can define a complete perimeter with at least a portion of the inner surface having a dimension greater than the outer dimension of tulip head 106 and which can fit over the upper portion of tulip head 106. First portion 12 can have extensions or slots that snap into pockets 114 or over protrusions, respectively, of the tulip head 106 to join and/or connect converter member 10 to tulip head 106. Inner surface 14 defines an opening 18 that surrounds and defines a first portion axis A1, which in use can be coaxial with the set screw 124 axis of tulip head 106. That is, first portion axis A1 can be considered to be oriented generally vertically. In an embodiment, a first portion set screw 40 (not shown) can be secured through first portion 12 of converter member 10 to internal threads 116 of tulip head for securement, or additional securement, to join the converter member 10 to tulip head 106. The first portion set screw 40 can be effectively counter-sunk into the first portion 12 of converter member 10 and provide for secure joining of the converter member 10 to the tulip head 106. First portion set screw 40 can additionally supply securement forces against spinal fixation rod 124.

Second portion 20 can extend downwardly from first portion 12 and can include a shaped surface 22 for contacting and/or securing spinal fixation rod 122. The shaped surface 22 can be a generally smooth, partial cylindrical-shaped surface defining a central axis A2. The shaped surface 22 can have dimensions that enable close contact with the spinal fixation rod 122 when joined to a tulip head 106.

As with the embodiment illustrated in FIG. 7, in an embodiment, shaped surface 22 can have a shaped extension 24 that wraps at least an included angle ANG1 of from 10 degrees to 100 degrees measured from a plane P1 in which lies axis A2 and which is perpendicular to axis A1. As can be understood from the description herein, shaped extension can partially wrap spinal fixation rod 122 when converter member 10 is seated and engaged and/or joined to tulip head

106. Secure snapping to pockets or protrusions of tulip head 106 and/or secure tightening of first portion set screw 40 secures converter member to tulip head 106 for final fixation and conversion of an open style tulip head pedicle screw to a pedicle screw having a closed head.

An open style tulip head pedicle screw can be converted to a closed style pedicle screw prior to insertion of a spinal fixation rod. In general, the conversion can be achieved by methods for converting an open style tulip had pedicle screw to a closed style pedicle screw, as disclosed herein, and as illustrated in the process 140 described with reference to FIG. 14. At step 142, an open style tulip head of a pedicle screw having internal threads defining a set screw axis can be provides. The open style tulip head can have an upper surface and a channel-like opening extending from the opening to a rod seat surface, wherein the channel-like opening includes internal threads for receiving a tulip head set screw along a tulip head set screw axis. At step 144 converter member as disclosed herein can be provided. The converter member can include a first portion joined to a second portion, the first portion having a surface parallel to a first portion plane, and an opening defining a first portion axis. The converter member can include a first portion having a first portion axis and a second portion extending from the first portion the second portion having a second portion axis that is perpendicular and coplanar with the first portion axis. The second portion can extend from the first portion and have a surface parallel to a second portion plane. The second portion plane can be perpendicular to the first portion plane, the second portion having a curved surface that defines a second portion axis, the second portion axis being perpendicular to and coplanar with the first axis. At step 146 the converter member can be mated to the open style tulip head by translating the converter member onto the open style tulip head such that the first portion axis is aligned with the tulip head set screw axis. Optionally, at step 148, a set screw can be provided and used to screw into the internal threads of the open style tulip head to secure the converter member to the open style tulip head.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

The invention claimed is:
1. A pedicle screw tulip head converter, the converter comprising:
    a first portion and a second portion extending from the first portion,
        the first portion having a surface parallel to a first portion plane, and an opening defining a first portion axis perpendicular to the first portion plane, the second portion having a surface and a second portion threaded opening, the second portion having a partial cylindrical-shaped surface that defines a second portion axis, the second portion axis being perpendicular to and coplanar with the first portion axis;

wherein when the first portion is installed on a pedicle screw tulip head, the second portion axis is coaxial with an axis of a spinal rod channel of the pedicle screw tulip head.

2. The pedicle screw tulip head converter of claim 1, wherein the opening comprises internal threads.

3. The pedicle screw tulip head converter of claim 1, further comprising a second portion set screw having external threads, and wherein the second portion threaded opening comprises internal threads and the external threads of the second portion set screw threadingly engaged to the internal threads in a direction offset and parallel to the first portion axis.

4. The pedicle screw tulip head converter of claim 1, wherein the partial cylindrical-shaped surface comprises a shaped extension that extends from the partial cylindrical-shaped surface a distance sufficient to traverse at least an included angle of from 10 degrees to 90 degrees measured from a plane in which lies the second portion axis and which is perpendicular to the first portion axis.

5. A method for converting an open style tulip head pedicle screw to a closed style pedicle screw, the method comprising the steps of:

providing an open style tulip head of a pedicle screw, the open style tulip head having an upper surface and a channel-like opening extending from an opening to a rod seat surface, wherein the channel-like opening includes internal threads for receiving a tulip head set screw along a tulip head set screw axis;

providing a converter implant, the converter implant comprising:

a first portion and a second portion extending from the first portion, the first portion having a surface parallel to a first portion plane, and a first portion opening defining a first portion axis perpendicular to the first portion plane, and the second portion having a surface parallel to a second portion plane and a second portion threaded opening, the second portion plane being perpendicular to the first portion plane, the second portion having a partial cylindrical-shaped surface that defines a second portion axis, the second portion axis being perpendicular to and coplanar with the first portion axis; and joining the converter implant onto the open style tulip head such that the first portion axis is aligned with the tulip head set screw axis and the second portion axis is coaxial with an axis of a spinal rod when the spinal rod is positioned within a spinal rod seat of the pedicle screw tulip head.

6. The method of claim 5, wherein the joining step comprises inserting the tulip head set screw through the first portion opening and screwing the tulip head set screw into the internal threads.

7. The method of claim 5, wherein the second portion threaded opening comprises internal threads and the converter implant further comprises a second portion set screw threaded on the internal threads in a direction offset and parallel to the first portion axis.

8. A pedicle screw tulip head converter, the converter comprising:

a first portion having a surface parallel to a first portion plane, and a first portion opening defining a first portion axis perpendicular to the first portion plane; and a second portion comprising a first lobe extending from a first side of the first portion and a second lobe extending from a second side of the first portion such that the first and second lobes are in a spaced apart, parallel relationship with each other, each of the first and second lobes have a closed perimeter forming respective first and second lobe openings having coaxial alignment;

wherein when the pedicle screw tulip head converter is installed on a pedicle screw tulip head, the first and second lobe openings are positioned on opposite sides of the pedicle screw tulip head and are coaxial with an axis of a spinal rod channel of the pedicle screw tulip head.

9. The pedicle screw tulip head converter of claim 8, wherein when a spinal rod is seated in a spinal rod seat of the pedicle screw tulip head and the pedicle screw tulip head converter is positioned upon the pedicle screw tulip head, the first and second lobe openings encompass the spinal rod and are coaxial with an axis of the spinal rod.

10. The pedicle screw tulip head converter of claim 8, wherein the first and second lobes extend from the first portion perpendicular to the first portion plane.

11. The pedicle screw tulip head converter of claim 10, wherein the first and second lobe openings have a lobe axis that when installed on the pedicle screw tulip head is coaxial with the tulip head channel axis.

12. The pedicle screw tulip head converter of claim 11, wherein when the pedicle screw tulip head converter is positioned upon the pedicle screw tulip head, the first portion surface extends at least partially over an upper opening of the pedicle screw tulip head channel.

13. The pedicle screw tulip head converter of claim 11, wherein the first portion opening comprises internal threads.

14. A pedicle screw tulip head converter, the converter comprising:

a first portion and a second portion extending from the first portion, the first portion having a surface parallel to a first portion plane, and an opening defining a first portion axis perpendicular to the first portion plane, the second portion having a surface parallel to a second portion plane, the second portion plane being perpendicular to the first portion plane, the second portion having a partial cylindrical-shaped surface that defines a second portion axis, the second portion axis being perpendicular to and coplanar with the first portion axis;

wherein when the first portion is installed on a pedicle screw tulip head, the second portion axis is coaxial with an axis of a spinal rod channel of the pedicle screw tulip head;

wherein the partial cylindrical-shaped surface comprises a shaped extension that extends from the partial cylindrical-shaped surface a distance sufficient to traverse at least an included angle of from 10 degrees to 90 degrees measured from a plane in which lies the second portion axis and which is perpendicular to the first portion axis.

15. A method for converting an open style tulip head pedicle screw to a closed style pedicle screw, the method comprising the steps of:

providing an open style tulip head of a pedicle screw, the open style tulip head having an upper surface and a channel-like opening extending from an opening to a rod seat surface, wherein the channel-like opening includes internal threads for receiving a tulip head set screw along a tulip head set screw axis;

providing a converter member, the converter member comprising:

a first portion and a second portion extending from the first portion, the first portion having a surface parallel to a first portion plane, and a first portion opening defining a first portion axis perpendicular to the first portion plane, and the second portion having a surface parallel to a second portion plane, the second portion plane being perpendicular to the first portion plane, the second portion having a shaped surface that defines a second portion axis, the second portion axis being perpendicular to and coplanar with the first portion axis; and joining the converter member onto the open style tulip head such that the first portion axis is aligned with the tulip head set screw axis and the second portion axis is coaxial with an axis of a spinal rod when the spinal rod is positioned within a spinal rod seat of the pedicle screw tulip head;

wherein the second portion comprises a first lobe and a second lobe, wherein each of the first and second lobes comprises a closed perimeter defining an enclosed opening.

16. A cap-style converter, the converter comprising:

a first portion configured to cover and partially surround a tulip head, and a second portion integrally-formed with the first portion--has been inserted;

the second portion comprising an integrally-formed circular-shaped lip, the lip configured to completely surround the tulip head, the lip having an internal surface; and external threads extending downwardly from the first portion and interiorly to and coaxial with the second portion, the external threads spaced inwardly a sufficient distance to permit a portion of the tulip head to extend between the external threads and the interior surface of the lip;

wherein the external threads are configured to engage internal threads of the tulip head.

\*   \*   \*   \*   \*